US00PP34260P3

(12) United States Plant Patent
Kordes

(10) Patent No.: US PP34,260 P3
(45) Date of Patent: May 24, 2022

(54) FLORIBUNDA ROSE PLANT NAMED 'KOROUTOFKO'

(50) Latin Name: *Rosa hybrida*
Varietal Denomination: KORoutofko

(71) Applicant: W. KORDES' SÖHNE Rosenschulen GmbH & Co KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 17/477,210

(22) Filed: Sep. 16, 2021

(65) Prior Publication Data

US 2022/0087089 P1 Mar. 17, 2022

(30) Foreign Application Priority Data

Sep. 17, 2020 (QZ) ..... PBR 20202202

(51) Int. Cl.
*A01H 5/02* (2018.01)
*A01H 6/74* (2018.01)

(52) U.S. Cl.
USPC ..... Plt./151
CPC ..... *A01H 6/749* (2018.05)

(58) Field of Classification Search
USPC ..... Plt./108, 150, 151, 139, 140
CPC ... A01H 5/02; A01H 5/00; A01H 6/74; A01H 6/749
See application file for complete search history.

(56) References Cited

U.S. PATENT DOCUMENTS

PP23,159 P2 11/2012 Kordes
PP23,549 P3 * 4/2013 Sproul ..... A01H 5/02 Plt./108

OTHER PUBLICATIONS

CPVO Register version 4.1.12 for 'Koroutofko', retrieved on Oct. 20, 2021, retrieved from the Internet at https://online.plantvarieties.eu/publicSearch?denomination=koroutofko, 3 pp. (Year: 2021).*
Kordes Roses Novelties 2020/2021 & Collection, retrieved on Oct. 20, 2021, retrieved from the Internet at https://www.rosen.de/download/Kordes-Roses_Collections-2021.pdf, cover page, pp. 6 and 22. (Year: 2021).*

* cited by examiner

*Primary Examiner* — June Hwu
(74) *Attorney, Agent, or Firm* — Panitch Schwarze Belisario & Nadel LLP; Stephany G. Small; Travis W. Bliss

(57) ABSTRACT

A new and distinct variety of floribunda rose plant, referred to by its cultivar name, 'KORoutofko', is disclosed. The new variety forms abundantly on a substantially continuous basis attractive, dark red colored blossoms. Attractive vigorous vegetative is formed, which contrasts beautifully with the blossoms. The growth habit is very bushy. The new variety is well suited for providing attractive ornamentation in the landscape.

1 Drawing Sheet

Latin name of genus and species of plant claimed: *Rosa hybrida.*

Variety denomination: 'KORoutofko'.

CROSS REFERENCE TO RELATED APPLICATIONS

This application claims priority to Plant Breeders' Right Application Number 20202202, which was filed at Community Plant Variety Office in the European Union on Sep. 17, 2020, the contents of which are hereby incorporated by reference for all purposes.

BACKGROUND OF THE INVENTION

The new variety of floribunda rose plant of the present invention was created by controlled breeding in May 2007 in Sparrishoop, Germany by artificial pollination wherein two parents were crossed which previously had been studied in the hope that they would contribute the desired characteristics. The female parent (i.e., the seed parent) of the new variety was 'KORmarkron' (U.S. Plant Pat. No. 23,159). The male parent (i.e., the pollen parent) of the new variety was an unnamed breeder seedling (non-patented).

The parentage of the new variety can be summarized as follows:

'KORmarkron' X unnamed breeder seedling

The seeds resulting from the above pollination were sown and small plants were obtained which were physically and biologically different from each other. Selective study resulted in the identification of a single plant of the new variety.

The new variety has been found to undergo asexual propagation in Cochranville, Pa. by a number of routes, such as vegetative cuttings. Asexual propagation techniques in Cochranville, Pa., such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of floribunda rose plant of the present invention possesses the following combination of characteristics:

(a) displays attractive, dark red colored blossoms,
(b) exhibits a very bushy growth habit,
(c) forms vigorous vegetation, and
(d) provides glossy, dark green foliage.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'KORmarkron' variety (i.e., the seed parent) displays more petals, a less bushy growth habit, and brighter red colored flowers compared to the new variety. In addition, the unnamed breeder seedling male parent (i.e., the pollen parent) displays less petals and a less bushy growth habit compared to the new variety. Moreover, the new variety can be readily distinguished from other similar non-parental varieties. For example, the 'Sprothrive' variety (U.S. Plant Pat. No. 23,549) displays larger sized leaflets compared to the new variety and exhibits red-colored styles, whereas the new variety exhibits yellow-colored styles.

The new variety has been named 'KORoutofko'.

BRIEF DESCRIPTION OF THE PHOTOGRAPHS

The accompanying photograph shows, as nearly true as it is reasonably possible to make the same in color illustrations of this character, typical specimens of the new variety. The illustrated rose plant of the new variety was approximately four years of age and was observed at Cochranville, Pa., U.S.A. while growing outdoors in the ground on its own roots.

Drawing—illustrates a specimen of a plant displaying blossoms.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a four-years-old specimen of the new variety, observed during June, while growing on its own roots outdoors and in the ground in Cochranville, Pa.

Commercial classification: Floribunda Rose Plant.

Plant:

*Habit*.—Very bushy and rounded.
*Height*.—Approximately 3.5 feet on average.
*Width*.—Approximately 3.5 feet on average.

Branches:

*Stem color*.—Commonly near Yellow-Green Group 144A.
*Length*.—Main stems: approximately 72.0 cm on average. — secondary stems: approximately 20.0 cm on average.
*Diameter*.—Main stems: approximately 5.0 mm on average. — secondary stems: approximately 3.0 mm on average.
*Young shoots*.—Anthocyanin coloration: absent.
*Thorns*.—Amount: moderate, 3 to 4 thorns per internode. — young thorns: color is commonly near Greyed-Orange Group 163A; length is approximately 3.0 mm on average; and width is approximately 2.0 mm on average at point of attachment. — old thorns: color is commonly near Greyed-Orange Group 166B; length is approximately 5.0 mm on average; and width is approximately 7.0 mm on average at point of attachment.

Foliage:

*Young foliage color*.—Upper surface: commonly near Yellow-Green Group 146A with indistinguishable venation. — under surface: commonly near Yellow-Green Group 146C with indistinguishable venation.
*Old foliage color*.—Upper surface: commonly near Green Group 139A with indistinguishable venation. — under surface: commonly near Yellow-Green Group 146C with indistinguishable venation.
*Petiole*.—Upper and under surfaces: texture is smooth; color is commonly near Green Group 138A. — length: approximately 3.0 cm on average. — diameter: approximately 1.0 mm on average.
*Rachis*.—Color: upper surface is commonly near Green Group 137A, under surface is commonly near Yellow-Green Group 144A; length is approximately 6.0 cm on average; diameter is approximately 1.0 mm on average.
*Stipules*.—Length: approximately 2.0 mm on average. — width: approximately 4.0 mm on average. — margin: entire to erose. — color: upper and under surfaces are commonly near Yellow-Green Group 144A.
5-*leaflet leaf*.—Length: approximately 12.0 cm on average. — width: approximately 10.0 cm on average.

Leaflets:

*Number of leaflets*.—3, 5, and 7.
*Shape*.—Ovate; apex is acute to acuminate; and base is rounded.
*Leaflet margin*.—Serrate, undulation is medium.
*Glossiness of upper side of leaflet*.—Glossy, intensity of leaflet glossiness is strong.
*Texture*.—Upper and under surfaces is smooth.
*Terminal leaflet*.—Length: approximately 6.0 cm on average. — width: approximately 3.0 cm on average.
*Lower leaflet*.—Length: approximately 2.8 cm on average. — width: approximately 1.7 cm on average.

Inflorescence:

*Number of flowers*.—Generally about 40 blooms open on average on a plant at once.
*Number of blooms per stem or in a cluster*.—Typically between four to five blooms per stem on average.
*Blooming season*.—Typically in bloom outdoors from May to November in Southeastern Pennsylvania.
*Peduncle*.—Length: approximately 3.0 cm on average. — diameter: approximately 2.0 mm on average. — surface texture: smooth. — color: commonly near Green Group 143A.
*Sepals*.—Number: commonly 5. — length: approximately 2.5 cm on average. — width: approximately 8.0 mm on average. — margin: entire with extensions on two or three sepals measuring approximately 5.0 mm in length on average and 1.0 mm in width on average. — upper surface color and texture: commonly near Green Group 143A; covered in short pubescence. — under surface color and texture: commonly near Yellow-Green Group 148B; puberulent. — apex: acute to aristate. — base: truncate as it joins the receptacle.

*Bud*.—Shape: ovoid. — length: approximately 1.5 cm on average. — width: approximately 1.4 cm on average. — color when opening: commonly near Red Group 53A.

*Flower*.—Diameter: approximately 6.0 cm on average. — height: approximately 2.0 cm on average. — duration: flower is on the plant approximately 8-10 days. — form: double, cuplike. — profile: convex to flat as it opens. — number of petals under normal conditions: approximately 12 petals on average. — shape of the petal: overall: broadly obovate. apex: rounded. base: cuneate. — petal length: approximately 2.4 cm on average. — petal width: approximately 2.5 cm. — petal margin: entire with moderate to strong undulation. — petal drop: excellent. — fragrance: none noticeable. — petal color when first and fully opened: upper surface: commonly between near Red Group 46A and 46B, basal spot is very small and commonly near White Group NN155A. under surface: commonly near Red Group 46B. — petal color at end of blooming: upper surface: commonly near Red Group 46C with some coloration of 187A towards the petal margins. under surface: commonly near Red Group 53C. — petal texture: upper and lower surfaces are glabrous. — petaloids: typically 1 or 2 per flower; color is commonly between near Red Group 46A and 46B; length is approximately 1.5 cm on average; width is approximately 5.0 mm on average.

*Receptacle*.—Color: commonly near Green Group 143A. — diameter: approximately 6.0 mm on average. — depth: approximately 5.0 mm on average. — surface texture: smooth. — shape: urn shaped.

*Stamen*.—Number is approximately 160 on average. — anthers: number is approximately 160 on average; color is commonly near Yellow-Orange Group 22A; length is approximately 3.0 mm on average; and shape is oval. — filaments: length is approximately 3.0 mm on average and color is commonly near Orange-Red Group 34B.

*Pistils*.—Arrangement is separate and free; number is approximately 60 on average. — styles: length is approximately 4.0 mm on average and color is commonly near Yellow Group 3C. — stigmas: diameter is approximately 1.0 mm; color is commonly near Yellow Group 3C; shape is fan shaped.

*Pollen*.—None observed.

*Hips/seed formation*.—None observed.

Development:

*Vegetation*.—Glossy, dark green, vigorous, and strong.

*Blossoming*.—Abundant and substantially continuous from spring through frost.

*Hardiness*.—Hardy to USDA Zone 5.

*Resistance to disease*.—Very good resistance to powdery mildew (*Sphaerotheca pannosa*) and black spot (*Diplocarpon rosae*) disease under normal greenhouse growing conditions in Cochranville, Pa.

Plants of the 'KORoutofko' variety have not been observed under all possible environmental conditions to date. Accordingly, it is possible that the phenotypic expression may vary somewhat with changes in light intensity and duration, cultural practices, and other environmental conditions.

I claim:

1. A new and distinct variety of floribunda rose plant named 'KORoutofko' characterized by the following combination of characteristics:

(a) displays attractive, dark red colored blossoms, (b) exhibits a very bushy growth habit, (c) forms vigorous vegetation, and (d) provides glossy, dark green foliage;

substantially as herein shown and described.

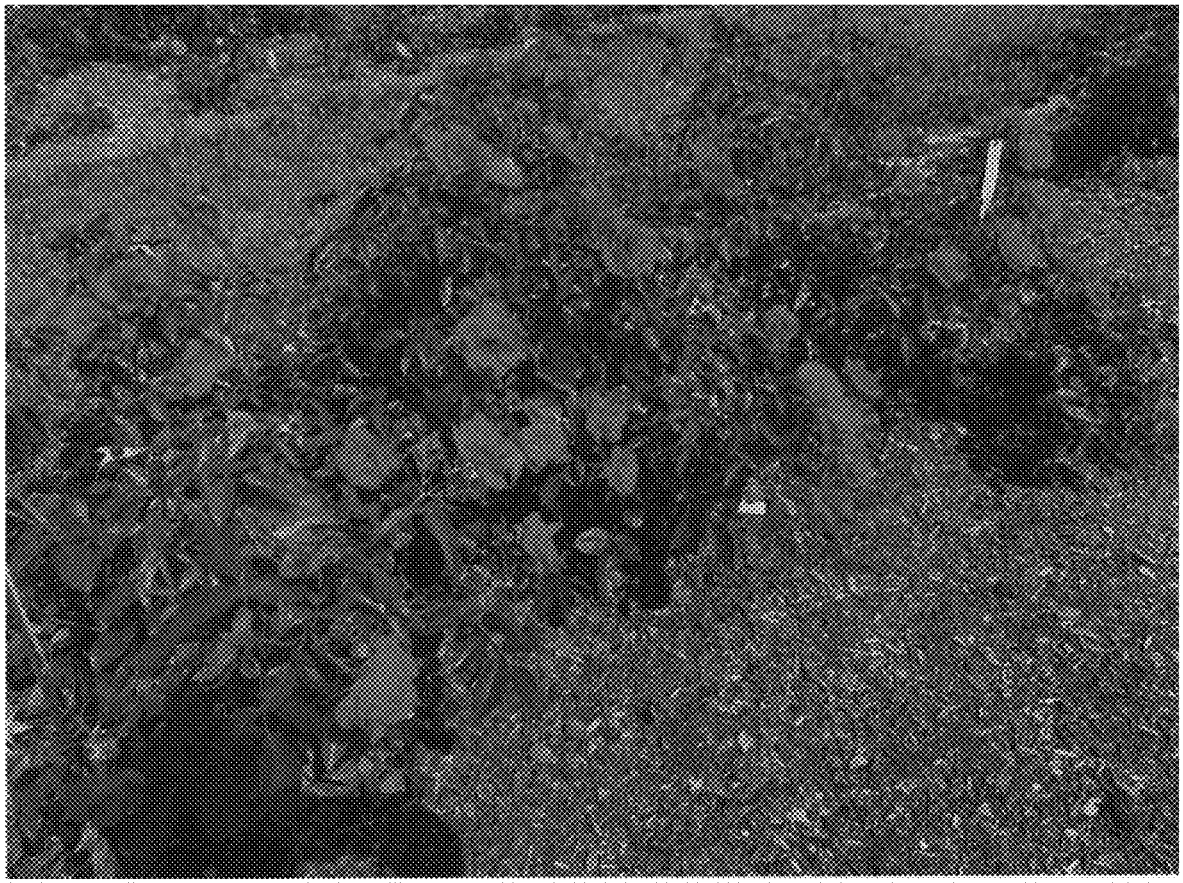

* * * * *